US00PP36681P2

(12) United States Plant Patent
Hansen

(10) Patent No.: US PP36,681 P2
(45) Date of Patent: May 13, 2025

(54) ***ECHINACEA* PLANT NAMED 'Everything's Rosy'**

(50) Latin Name: ***Echinacea* hybrid**
Varietal Denomination: Everything's Rosy

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,338

(22) Filed: Nov. 22, 2024

(51) Int. Cl.
*A01H 5/02* (2018.01)
*A01H 6/14* (2018.01)

(52) U.S. Cl.
USPC ..... Plt./428

(58) Field of Classification Search
USPC ..... Plt./428

CPC ..... A01H 5/02; A01H 5/00; A01H 6/1448; A01H 6/14
See application file for complete search history.

(56) References Cited

U.S. PATENT DOCUMENTS

PP24,458 P2 * 5/2014 Blom ..... A01H 6/14 Plt./428
PP35,462 P2 * 11/2023 Hansen ..... A01H 6/1448 Plt./428

* cited by examiner

*Primary Examiner* — June Hwu

(57) ABSTRACT

The new and distinct cultivar of *Echinacea* plant named 'Everything's Rosy' of heavily-branched, strong, upright stems, producing faintly fragrant inflorescences with wide ray florets of pinkish-lavender color. The rosy-colored disk florets produce a large center pompon. The new plant has dark-green ovate foliage, produces flowers from mid-summer to late summer, and is suitable as a potted plant, for the landscape, and for cut flower arrangements.

1 Drawing Sheet

Botanical denomination: *Echinacea* hybrid.
Cultivar designation: 'Everything's Rosy'.

STATEMENT REGARDING PRIOR DISCLOSURES UNDER 37 CFR 1.77(B)(6)

The first non-enabling disclosures of the claimed plant, in the form of a photograph and brief description on a website operated by Walters Gardens, Inc. on Dec. 1, 2023, followed by a photograph and brief description in the "Walters Gardens 2024-2025 Catalog" on May 23, 2024. The claimed plant was first offered for sale on Dec. 4, 2023, to Sooner Plant Farms by Walters Gardens, Inc. who obtained the plant and all information about the plant from the inventor. No plants of *Echinacea* 'Everything's Rosy' have been sold in this country or anywhere in the world, nor has any disclosure of the new plant been made, more than one year prior to the filing date of this application, and such sale or disclosure within one year was either derived directly or indirectly from the inventor and therefore a 35 U.S.C. § 102(b) exception.

BACKGROUND OF THE INVENTION

The present invention relates to the new and distinct cultivar of Coneflower from the genus *Echinacea* and given the cultivar name 'Everything's Rosy'. The new plant was the result of a cross by the inventor of an unnamed proprietary hybrid known as 18-28-5 (not patented) as the female parent and an unnamed proprietary hybrid known as 18-17-1 (not patented) as the male in the summer of 2019, at a wholesale perennial nursery in Zeeland, Michigan. The single seedling selected was evaluated initially in trials in the summer of 2020 at the same nursery and assigned the breeder code of 19-6-5.

*Echinacea* 'Everything's Rosy' has been asexually propagated at the same nursery by crown division and also using careful shoot tip tissue culture procedures and found to reproduce plants that exhibit all the characteristics identical to the original plant in successive generations.

*Echinacea* 'Everything's Rosy' is distinct from all other Coneflowers known to the inventor. The nearest comparison cultivars are: 'Butterfly Kisses' U.S. Plant Pat. No. 24,458, 'Strawberry Mouse' (not patented), 'Razzmatazz' U.S. Plant Pat. No. 13,894, 'Delicious Candy' (not patented), 'Rainbow Sherbet' U.S. Plant Pat. No. 35,462 and 'Secret Affair' U.S. Plant Pat. No. 24,354.

'Butterfly Kisses' has a shorter habit with smaller inflorescences having light-pink ray florets and lighter rose disk florets that stay close to the same colors through maturity. 'Strawberry Mousse' is taller in habit, with larger inflorescences having ray florets of a lighter pinkish color that droop more, and the disk pompon is lighter purplish-pink. 'Razzmatazz' is much taller in habit, has peduncles with less branching, smaller inflorescences with light pinkish-purple ray florets that droop more, and a slightly lighter colored center pompom. 'Delicious Candy' has smaller inflorescences, the horizontally-held ray florets are a bright fuchsia color, and the disk florets are a reddish-orange. 'Secret Affair' has a less branching habit, inflorescences with a single row of more drooping ray florets with a deeper purplish-red color, and the center pompon has larger disk florets with more reddish-purple color. 'Rainbow Sherbet' has a taller habit and more orangish-red ray florets when initially opening that mature to a more coral pink.

The female parent plant, 18-28-5, has a taller habit with less basal branching and double rows of ray florets of a salmon-pink. The male parent plant, 18-17-1, has less basal branching, double rows of ray florets or rosy-reddish color. Neither of the parents have ray florets that are as imbricate as the new plant.

SUMMARY OF THE INVENTION

*Echinacea* 'Everything's Rosy' has not been evaluated under all possible environmental conditions. The phenotype may vary with variations in the environment including: growing temperature, available sunlight, nutrients, water, etc. without a change in the genotype of the plant. The new plant is distinct from its parents and all other *Echinacea* known to the applicant in the following combined traits:

1. Fragrant inflorescences with pinkish-lavender ray florets;
2. Center pompon of rosy-colored disk florets;
3. Vigorous, compact, growth habit with heavy branching, and strong stems;
4. Dark-green ovate foliage.

BRIEF DESCRIPTION OF THE DRAWINGS

The photographs of 'Everything's Rosy' demonstrate the overall appearance of the plant including the unique traits. The drawings of the new plant are of a two-year-old plant grown in a full-sun trial garden in Zeeland, Michigan. The colors are as accurate as reasonably possible with color reproductions. Some slight variations of color may occur as a result of lighting quality, intensity, wavelength, direction, or reflection.

Figure 1:
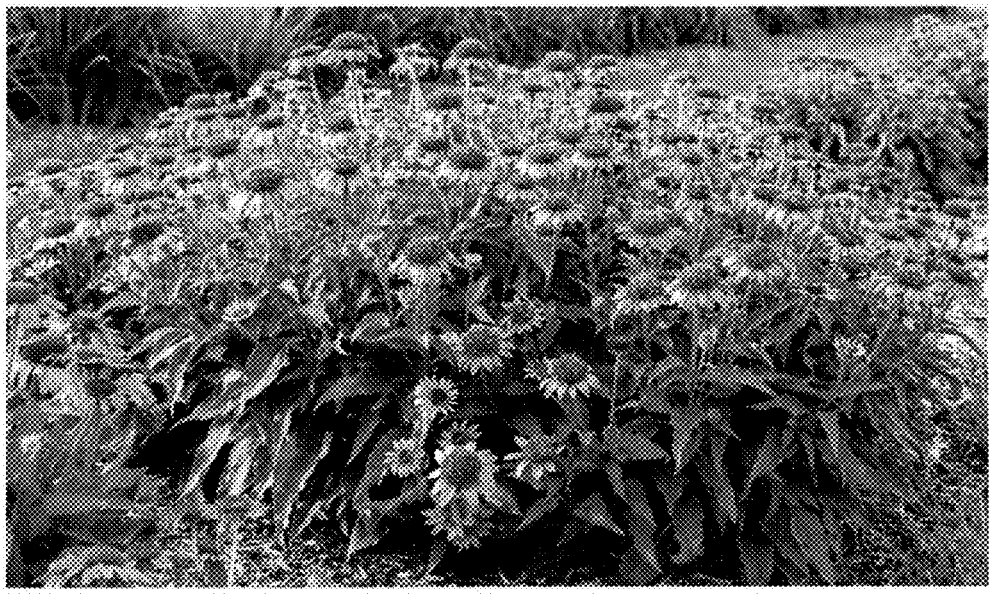
FIG. 1 shows the landscape habit of the new plant in the flower.
Figure 2:
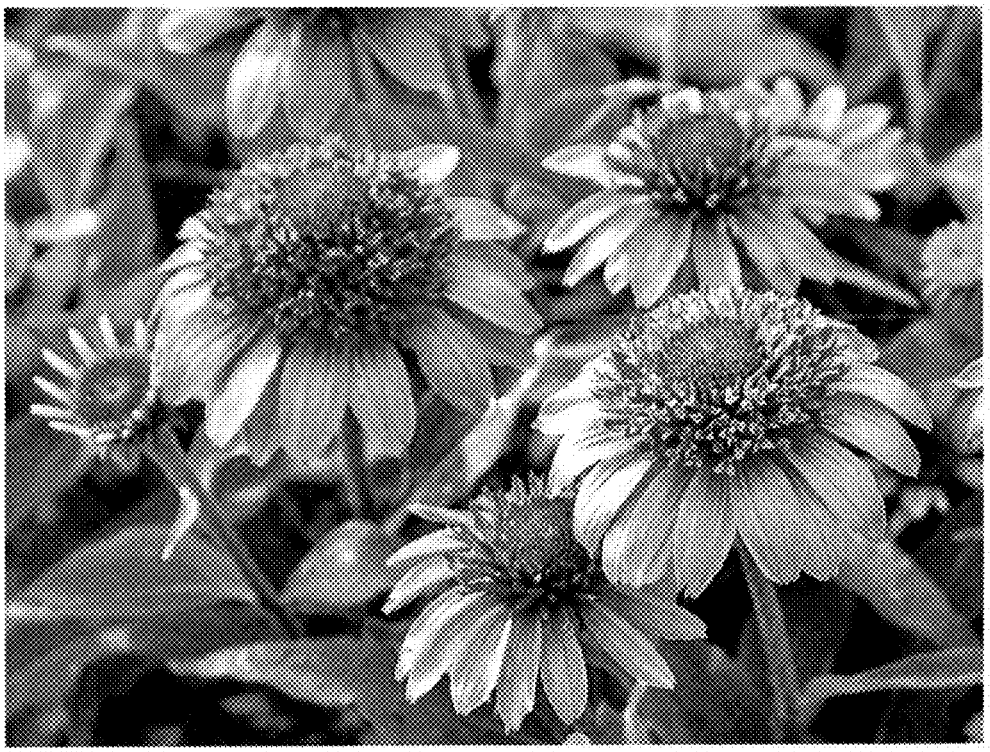
FIG. 2 shows a close-up of some inflorescences with ray florets at various stages of color and large center pompon.

DETAILED DESCRIPTION OF THE PLANT.

The following description of *Echinacea* 'Everything's Rosy' is based on observations of two-year-old specimens grown in a partially-shaded greenhouse and an open sun trial area in Zeeland, Michigan. The new plant has not been tested in all environments and some phenotypic differences may occur with different environments without, however, any change in genotype. The color descriptions are based on the 2015 edition of The Royal Horticultural Society Colour Chart except where common dictionary descriptions are used.

Parentage: Female or seed parent is the proprietary unreleased hybrid 18-28-5 and male parent is the proprietary unreleased hybrid 18-17-1; both parents comprising complex crosses with 'Solar Flare' U.S. Plant Pat. No. 22,133, 'Little Annie' (not patented), and 'Butterfly Kisses' U.S. Plant Pat. No. 24,458;

Plant habit: Multi-stemmed, freely-branched, hardy herbaceous perennial, flowering to about 54 cm tall and 43 cm wide with foliage to 52 cm tall and 43 cm wide;

Growth rate: Vigorous, finishing from a 25 mm plug in 3.8-liter containers in about 18 weeks during the summer;

Roots: Cream-colored, finely-branched;

Foliage: Alternate; ovate; acute apex; cuneate base; margin entire and micro-ciliolate; micro-hirsutulous adaxial and abaxial; to about 13.5 cm long and 4.3 cm wide decreasing distally, average about 10 cm long and 3.5 cm wide;

Leaf color: Young leaves adaxial between RHS 137B and RHS 137A, abaxial nearest RHS 138A; mature leaves adaxial between RHS 139A and RHS NN137A, abaxial between RHS 137C and RHS NN137D; variegation absent;

Foliage fragrance: Not observed;

Venation: Pinnately; hirsutulous adaxial and abaxial; abaxial midrib and veins costate;

Vein color: Adaxial basal midrib and basal primary veins between RHS 154D and RHS 145C, distal primary veins and secondary veins nearest RHS 146D; abaxial midrib and primary veins nearest RHS 146C, secondary veins RHS 147B;

Petiole: Concavo-convex; glabrous adaxial; hirsutulous abaxial; to about 7 cm long and 11 mm wide at the semi-clasping base and 3 mm wide in middle of lowest leaves, distal foliage decreasing to nearly sessile;

Petiole color: Adaxial center nearest RHS 145B, margin nearest RHS 137A; abaxial center between RHS 146B and RHS 146A, edge between RHS 137B and RHS 137A;

Stem: Hirsutulous; terete, fistulous; strong; stiff; to about 60 cm long including peduncle and about 11 mm diameter at base; average 56 cm long and 6 mm diameter; about 14 per plant; aspect upright;

Stem color: Proximally between RHS N144D and RHS 146D, distally nearest RHS 146D;

Peduncle: Hirsutulous to pubescent; cylindrical; strong; stiff; branched; to about 10.5 cm long and 4 mm diameter above last leaves; quantity per stem about 11 to 12; aspect strongly ascending;

Peduncle color: Nearest RHS 146D;

Node: 11 to 12 per stem; average internode about 4.6 cm long, longer in the middle; node color same as surrounding peduncle;

Branches: Cylindrical; hirsutulous; tightly angled to main stem to about 60° above horizontal: about six to ten branches per stem; to about 20 cm long and 4 mm diameter;

Branch color: Nearest RHS 146D;

Inflorescence: Bracteate head, aggregate of achene; with single whorl of distinct ligulate ray florets and enlarged disk florets above pappus producing a pompon effect; flowering mid-summer to late summer; initial inflorescence largest, to about 9.5 cm wide, with inner pompon to 5.5 cm across and 4 cm tall; typically six to ten inflorescences per stem;

Inflorescence fragrance: Faint, lightly sweet, honey-like;

Flower persistence: Remaining effective in color for 10 to 14 days depending on temperatures, cone drying on the plant, and effective into winter;

Involucre: With numerous bracts, about 60 to 72 per inflorescence in 3 to 4 whorls; reflex downward toward peduncle;

Involucre bracts: Deltoid; acute apex; truncate base; ciliolate margin; reflexed; adaxial glabrous to micro-puberulent; abaxial hirsutulous; to about 11 mm long and 3 mm across decreasing distally; color adaxial center nearest RHS 137C, adaxial edges between RHS 139A and RHS NN137B, and abaxial nearest RHS 137B;

Inflorescence buds with ray florets vertical and still enrolled: About 32 mm across and 20 mm tall; ray floret adaxial color nearest RHS 158A distally and between RHS 75C and RHS 76C proximally, abaxial color nearest RHS 6D distally and between RHS NN74D and RHS N75D proximally, disk florets nearest RHS 144A near center and perimeter nearest RHS 166B; disk florets to about 7 mm long, 2 mm wide near middle, and 1.5 mm wide at base;

Ray florets: Ligulate; zygomorphic; arrangement in a single moderately imbricate whorl; apex variably emarginated with two to three notches to 1 mm to 3 mm deep; base attenuate; margin entire; adaxial and abaxial surfaces matte and glabrous except basal 4 mm micro-puberulent abaxial; 16 to 22 per inflorescence; opening to horizontal, drooping up to 45 degrees below horizontal with maturity; flat, twisting or rolling absent; pistillate; ray floret ligule to 39 mm long and 16 mm wide near middle, base 2 mm wide; average size 35 mm long, 14 mm wide at center tapering to 2 mm wide at base; adaxial veins thickened and slightly sulcate;

Ray floret color: Changing with maturity; when first horizontal young adaxial nearest RHS N78B and abaxial between RHS N79D and RHS N78B; before dropping adaxial between RHS N77D and RHS 77C, abaxial between RHS 186D and RHS 77C; basal 2 mm remaining constant nearest RHS 146D in both adaxial and abaxial;

Disk florets: Numerous; about 400 to 500 per inflorescence; zygomorphic; perfect; produced in a large, raised dome about 5.5 cm across and 4 cm tall; individually to about 23 mm long, 3 mm across at apex, and 3 mm diameter at base;

*Disk floret corolla*.—Typically five tepals fused forming tube; to about 19 mm long and 6 mm wide at apex, fused in basal 14 mm, free in distal 5 mm; individual tepals about 3 mm wide at fusion; acute apex; entire margin; both surfaces slightly lustrous.

*Disk floret corolla tube color*.—Prior to opening center between RHS 186C and RHS 186B; upon first opening and at maturity color unchanged; adaxial nearest RHS 186B, and base nearest RHS 146D; abaxial between RHS 59C and RHS 60C with base between RHS 146C and RHS N186C.

*Androecium*.—Present on disk florets only; five; about 5 mm long, not exserted.

*Anthers*.—About 2 mm long and 0.5 mm diameter; color nearest RHS N199A.

*Filaments*.—Five; thin, less than 0.2 mm diameter and 3 mm long; color nearest RHS NN155A.

*Pollen*.—Not observed.

*Gynoecium*.—On ray and disk florets; single; to about 10 mm long.

*Style*.—Cylindrical; to about 4 mm long and 0.2 mm diameter; color nearest RHS 157D.

*Stigma*.—Bifid; about 2 mm long and 0.1 mm diameter; color nearest RHS 187A.

*Ovary*.—Inferior; obdeltoid; to 4 mm long and 1.5 mm wide at apex; color nearest RHS 146D distally and proximally nearest RHS 155B.

*Fruit*.—Not yet observed.

Receptacle spines: With disk florets; acicular; narrowly acute apex; glabrous; lustrous; to 13 mm long and 2 mm across near middle; producing a cone about 31 mm wide and 26 mm tall;

Spine color: Adaxial and abaxial apices nearest RHS 178B, distally between RHS 144A and RHS 144B, proximal portion translucent to nearest RHS 157D;

Disease resistance: Resistance and susceptibility beyond that of other hardy Coneflower cultivars have not been observed.

Growth: The plant grows best with plenty of moisture and adequate drainage but is able to tolerate some drought when mature.

Winter hardiness: at least from USDA zone 4 through 8.

I claim:

1. A new and distinct cultivar of *Echinacea* plant named 'Everything's Rosy' as herein described and illustrated.

* * * * *